United States Patent [19]

Schultze

[11] 4,141,364
[45] Feb. 27, 1979

[54] EXPANDABLE ENDOTRACHEAL OR URETHRAL TUBE

[76] Inventor: Jorge Schultze, 2550 Morgan Ave., Corpus Christi, Tex. 78405

[21] Appl. No.: 779,068

[22] Filed: Mar. 18, 1977

[51] Int. Cl.² .............................................. A61M 25/00
[52] U.S. Cl. .................................. 128/349 B; 128/4; 128/344; 128/351
[58] Field of Search ........................................ 128/4–8, 128/262, 343–345, 348–351

[56] References Cited

U.S. PATENT DOCUMENTS

| | | | |
|---|---|---|---|
| 2,548,602 | 4/1951 | Greenburg | 128/4 |
| 3,050,066 | 8/1962 | Koehn | 128/349 B |
| 3,502,069 | 3/1970 | Silverman | 128/262 X |
| 3,640,282 | 2/1972 | Kamen | 128/351 |
| 3,774,596 | 11/1973 | Cook | 128/5 |
| 3,911,927 | 10/1975 | Rich et al. | 128/349 R |

Primary Examiner—Dalton L. Truluck
Attorney, Agent, or Firm—G. Turner Moller

[57] ABSTRACT

There is disclosed an endotracheal tube which is collapsed transverse to the longitudinal dimension of the tube for insertion into the trachea of a patient. After the tube is in place, it is expanded to open an unobstructed passageway therethrough. An expandable cuff is provided on the exterior of the tube to afford a seal between the trachea and the tube. The same techniques are applicable to urethral catheters.

4 Claims, 9 Drawing Figures

EXPANDABLE ENDOTRACHEAL OR URETHRAL TUBE

This invention relates to tubes inserted into body passageways for delivering or withdrawing a fluid therethrough. More particularly, this invention relates to expandable and contractible tubes which are more readily inserted into body passageways and which incorporate an expandable cuff on the exterior thereof for sealing against the interior surface of the body passageway.

It is known in the art to provide an expandable cannula for insertion into a blood vessel of a patient as shown in U.S. Pat. No. 3,509,883.

Urethral catheters are widely used to drain the bladders of patients during surgery, for example, and in situations where normal bladder drainage is difficult. For example, enlarged prostate glands often substantially restrict the urethra thereby requiring catheterization.

Endotracheal tubes are widely used to provide intermittant anesthesia, air way patency or positive pressure respiration under many circumstances as shown, for example, in U.S. Pat. Nos. 3,173,418 and 3,948,273.

In preparation for a major surgical procedure, anesthesics are normally administered intravenously. One of the side effects of most modern anesthesics is that the involuntary nervous system controlling respiration is rendered inoperative. Accordingly, one of the major duties of the attending anesthesiologist is to establish mechanical breathing of the patient very quickly after the loss of consciousness because it is well known that failure of respiration commenses to cause irreversible brain damage in about five minutes. As a practical matter, the anesthesiologist has 2-3 minutes to insert an endotracheal tube into the trachea of the anesthesized patient, inflate the expandable cuff, hook up the mechanical respirator, and commence positive pressure breathing of the patient. If this is not accomplished within this time period, an anecdote to the anesthesic is intravenously administered to the patient so that normal breathing will commence before the lapse of five minutes. Under these circumstances, the patient comes out from under the anesthestic and the surgery must be postponed, usually for twenty-four hours.

It is accordingly evident that rapid and easy placement of an endotracheal tube is of considerable importance to the anesthesiologist, the surgeon, the operating room team and the hospital for a variety of reasons. Anesthesiologists are, of course, exceptionally well trained and exceptionally adept at inserting an endotracheal tube. However, because of the vast number of operations done in which general anesthestics are administered, it is evident that even a very small percentage of failures to promptly insert an endotracheal tube can create a substantial number of embarrassing and expensive surgical postponements. More importantly, a more reliable technique for inserting endotracheal tubes will undoubtedly reduce or minimize the possibility of patient brain damage.

As illustrated in the exemplary aforementioned United States patents, endotracheal tubes of the prior art comprise an elongate moderately flexible tube or conduit typically made of a rubber material and having an unobstructed or unvalved passageway therethrough. An expandable cuff is typically provided near the inserted end of the tube for sealing against the trachea. With a supine patient, the cuff is in a collapsed condition and the patient's head is moved downwardly as much as possible to provide a more-or-less straight path through the mouth and into the trachea. The endotracheal tube is inserted through the mouth until the inserted end thereof lies well within the trachea. The cuff is then expanded to seal against the trachea. The opposite end of the tube is then connected to a suitable pump alternately to force air or oxygen into the patient's lungs and to allow exhalation therefrom.

One of the difficulties with prior art endotracheal tubes is that many patients, typically those who are overweight or have short necks, cannot move their head downwardly from a horizontal position a sufficient distance to provide a substantially straight path from the mouth into the trachea. Although anesthesiologists are exceptionally adept at inserting endotracheal tubes, patients of this physical type present a substantial challenge to even the best and most experienced.

In endotracheal tubes of the prior art, there is an apparent compromise in the selection of the diameter of the tube or conduit. For insertion purposes, it is desirable that the tube be as small as practicable because a smaller tube would obviously be easier to insert. In operation, the diameter of the passage through the tube should be as large as possible to accommodate air movement into and out of the lungs with the least practicable restriction. It is apparent that with prior art designs, each of these desirable features must be compromised in favor of the other.

In the device of this invention, the endotracheal tube is collapsed transversely of the longitudinal dimension thereof for insertion into the patient's trachea. While in the trachea, the tube is expanded to provide a passage therethrough of substantial cross-sectional area. An inflatable cuff or other sealing means is expanded to provide a seal between the tube exterior and the trachea. Preferably, the tube comprises a pleated or corrugated conduit which is designed to collapse into an elongate body of minimal cross-sectional area. Encircling the air carrying conduit is an annulus providing member. The annulus is sealed at opposite ends thereof and a suitable controllable access is provided thereinto. The tube may be collapsed by evacuating the annulus around the conduit whereupon atmospheric pressure causes the conduit to collapse to its minimum dimension. After insertion into the trachea, the conduit is expanded to its normal dimension.

It is an object of this invention to provide an endotracheal tube which may be collapsed transversely of the longitudinal dimension thereof for insertion into a patient's trachea and then expanded while in the trachea to provide an unobstructed passage therethrough of considerable size.

IN THE DRAWINGS

Figure 1:
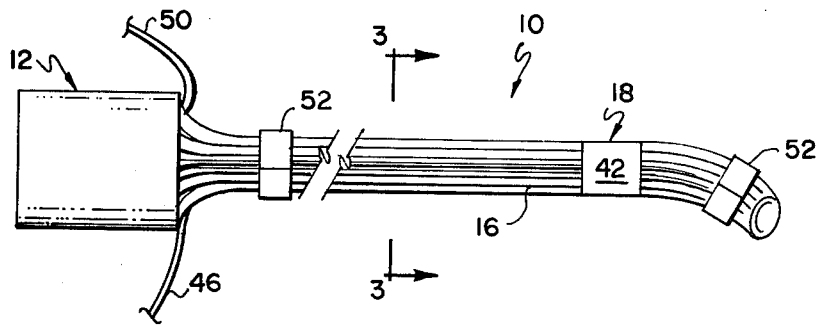
FIG. 1 is a side view of an endotracheal tube of this invention illustrated in the collapsed configuration thereof.
Figure 2:
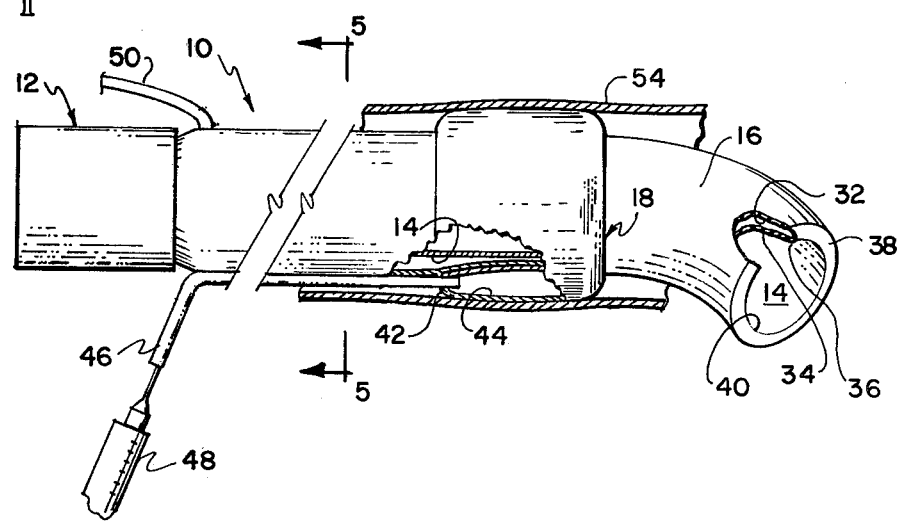
FIG. 2 is a partially broken view of the embodiment of FIG. 1 illustrating the tube in an expanded or operative position.

Referring to FIGS. 1 and 2, there is illustrated an endotracheal tube 10 of this invention comprising a fitting 12 for attachment to a suitable mechanical respirator, an inner conduit 14 for passing air toward and away from the fitting 12, an outer member 16 which is manipulated to allow the inner conduit 14 to expand and collapse, and a cuff 18 which may be of any suitable type. In overall length, the tube 10 is typically on the order of about 5-10 inches long.

Figure 4:
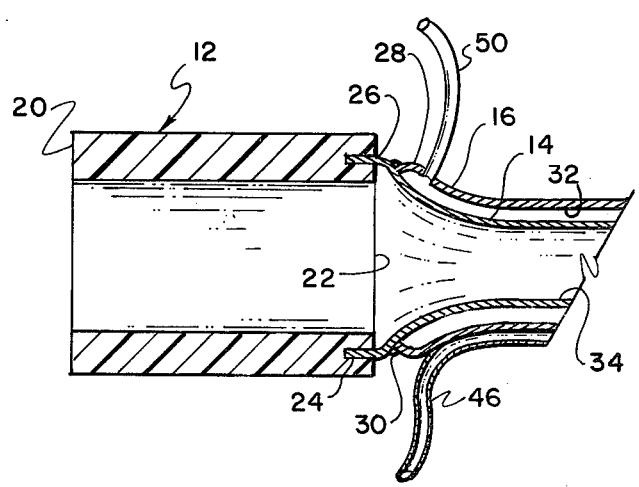
FIG. 4 is an enlarged cross-sectional view of the tube of FIGS. 1 and 3, taken substantially along line 4—4 of FIG. 3, as viewed in the direction indicated by the arrows.

As shown in FIG. 4, the fitting 12 conveniently comprises a short plastic tube preferably having a suitable quick-disconnect coupling (not shown) on the free end 20 thereof. The opposite fitting end 22 conveniently comprises a circular slot 24 receiving one end 26 of the inner conduit 14. A suitable adhesive material may be used to secure the conduit end 26 in the slot 24. One end 28 of the member 16 is affixed to and sealed against the conduit end 26 by suitable adhesive material 30. It will accordingly be apparent that the conduit 14 is in fluid transmitting relation with the fitting 12 and that an annulus 32 between the conduit 14 and the member 16 is sealed adjacent the fitting 12.

In lieu of the slot 24, the conduit end 26 and member end 28 may both be adhesively affixed to the fitting end 22. In the alternative, the conduit end 24 and the member end 26 may be rolled together and adhesively affixed in the slot 24.

Figure 3:
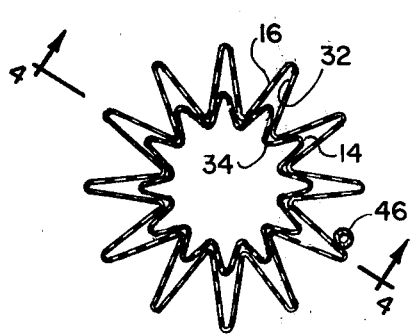
FIG. 3 is an enlarged cross-sectional view of the endotracheal tube of FIG. 1, taken substantially along line 3—3 thereof as viewed in the direction indicated by the arrows.
Figure 5:
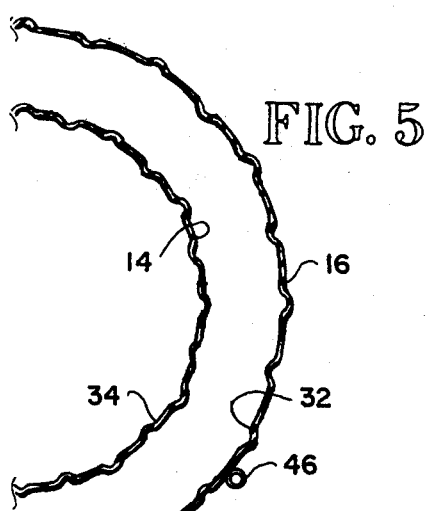
FIG. 5 is an enlarged cross-sectional view of the tube of FIG. 2, taken substantially along line 5—5 thereof and viewed in the direction indicated by the arrows.

As illustrated most clearly in FIGS. 3 and 5, the conduit 14 and member 16 comprise a pleated or corrugated body designed to collapse into a small cross-sectional area and expand to provide a fluid passage 34 therethrough of substantial cross-sectional area. The conduit 14 and member 16 are made of any suitable material having the desired characteristics. This material is preferably soft, pliable, resilient and having the capability of being extruded or otherwise formed in a pleated or corrugated configuration. In addition, in accordance with one embodiment of the invention, the material should have a memory, i.e. have the capability of moving from the collapsed position of FIG. 3 to the expanded position of FIG. 5 when the pressure in the passage 34 is substantially equal to the pressure in the annulus 32. Suitable materials include polyesters, rubber compounds and the like. One exemplary suitable material is silastic rubber.

Referring to FIG. 2, the conduit 14 and member 16 terminate in free end sections 36, 38 respectively and are sealed, as by the use of adhesives, heat sealing techniques or the like, along a circular trace 40 comprising an open end of the passage 34. It will be apparent that the passage 34, in the expanded position of the tube 10, is unvalved and unobstructed.

The cuff 18 may be of any suitable type and includes an inflatable diaphragm 42 sealed to the exterior of the tube 10 to provide, with the member 16, an inflatable annulus 44. A small tube 46 extends through the annulus 32 and provides communication between the annulus 44 and a location adjacent the fitting 12. In order to inflate the cuff 18, a syringe 48 is inserted into the end of the tube 46 and air is pumped into the annulus 44.

In order to collapse the tube 10, there is provided a conduit 50 providing communication with the annulus 32 at a location adjacent the fitting 12. During manufacture of the tube 10 or preparatory to use thereof, air is pumped out of the annulus 32 as by connecting a suitable vacuum pump to the conduit 50. The tube 10 accordingly collapses to the configuration shown in FIG. 3. Suitable strips 52 of cellophane or tape may be used to hold the conduit 14 and outer member 16 in the collapsed position during shipment.

In use, the tube 10 is removed from suitable packaging (not shown) and the strips 52 either removed or broken. While the tube 10 is in the collapsed configuration of FIGS. 1 and 3, the anesthesiologist inserts the same into the trachea 54 of the patient to be anesthesized. Air or any other suitable gas is then admitted into the conduit 50 to relieve the vacuum existing in the annulus 32. Because the conduit 14 and member 16 are made of a material having a memory, they return to their normal expanded position illustrated in FIGS. 2 and 5. The anesthesiologist then inflates the cuff 18 to seal between the exterior of the tube 10 and the trachea 54, connects the fitting 12 to a suitable mechanical respirator (not shown) and mechanical breathing is commenced.

It will be evident that the reduced diameter of the collapsed tube 10 facilitates the insertion thereof into the trachea 54. As is apparent from FIGS. 2 and 5, the fluid passage 34 is of substantial size to accommodate the required volume of air for respiration.

Referring to FIGS. 6-9, there is illustrated another embodiment 56 of this invention comprising a fitting 58 for attachment to a suitable mechanical respirator, an inner conduit 60 for passing air toward and away from the fitting 58, an outer member 62 which is manipulated to expand and collapse the inner conduit 60, and a cuff for sealing against a trachea 66 of the patient.

The fitting 58 conveniently comprises a short plastic tube preferably having a suitable quick-disconnect coupling (not shown) on the free end 68 thereof. The opposite fitting end 70 comprises a deep circular groove or slot 72 in communication with a radial passge 74 provided by a stub conduit or nipple 76 for purposes more fully explained hereinafter. One end 78 of the inner conduit 60 is affixed to and sealed against the wall of a passage 80 extending longitudinally of the fitting 58. To this end, the conduit end 78 may be adhesively secured to the passage 80 or an internal clamp 82 may be provided. One end 84 of the member 62 is affixed to and sealed against the outer circumference of the fitting 58 in any suitable manner, as by the use of adhesives or an external clamp 86. It will accordingly be apparent that the conduit 60 is in fluid transmitting relation with the fitting 58 and that an annulus 88 between the conduit 60 and member 62 is sealed adjacent the fitting 58.

Figure 7:
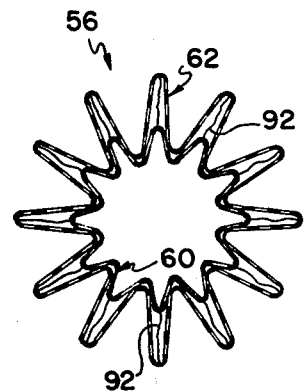
FIG. 7 is an enlarged cross-sectional view of the embodiment of FIG. 6, taken at a location similar to the illustration of FIG. 3, illustrating the tube in the collapsed position.
Figure 8:
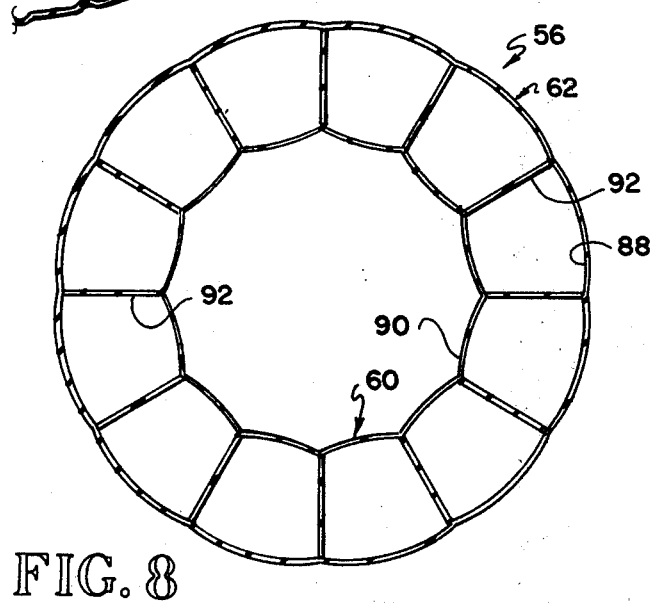
FIG. 8 is an enlarged cross-sectional view of the embodiment of FIG. 6 taken substantially along line 8—8 thereof as viewed in the direction indicated by the arrows.
Figure 9:
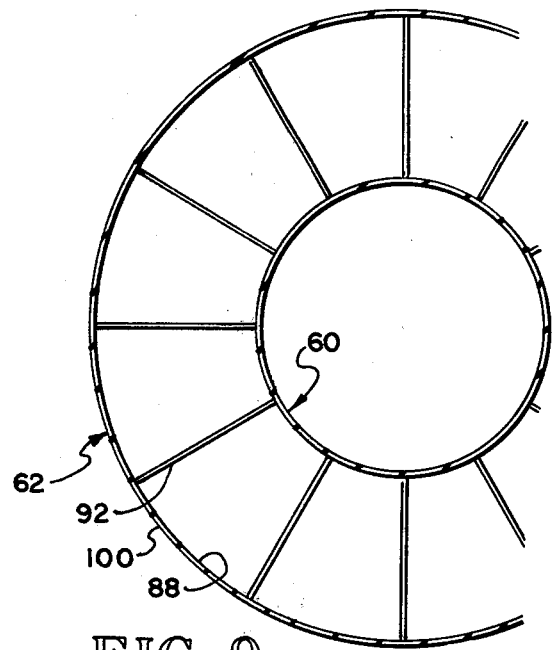
FIG. 9 is an enlarged cross-sectional view of the embodiment of FIG. 6 taken substantially along line 9—9 thereof as viewed in the direction indicated by the arrows.

As illustrated most clearly in FIGS. 7 and 8, the conduit 60 and member 62 comprise a longitudinally pleated or corrugated body designed to collapse into a small cross sectional area and to expand to provide a fluid passage 90 therethrough of substantial cross-sectional area. As in the embodiment of FIGS. 1–5, the conduit 60 and member 62 are made of a soft, pliable, resilient material capable of being extruded or otherwise formed in a pleated or corrugated configuration providing a plurality of generally equally spaced longitudinally extending struts or membranes 92 interconnecting the conduit 60 and member 62 for at least part of the length of the tube 56. One suitable exemplary material for the conduit 60 and member 62 is silastic rubber.

As will become more fully apparent hereinafter, the struts 92 divide the annulus 88 into a plurality of chord-shaped sections. Upon evacuation of the annulus 88, the tube 56 collapses into the configuration of FIG. 7 because of the existance of greater area exposed to atmospheric pressure by the member 62 than by the conduit 60. Upon the delivery of a gas at greater than atmospheric pressure into the annulus, the tube 56 expands because of the greater area exposed by the member 62 than by the conduit 60.

Figure 6:
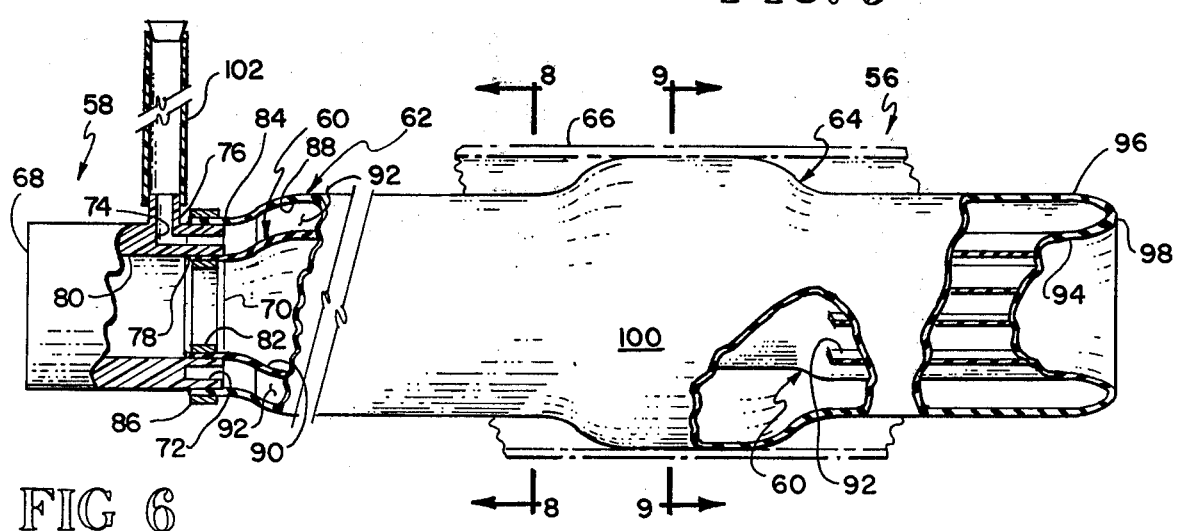
FIG. 6 is a partially broken side view of another embodiment of this invention illustrated in the expanded or operative condition thereof.

Referring to FIG. 6, the conduit 60 and member 62 terminate in free end sections 94, 96 respectively and are sealed, as by the use of adhesives, heat sealing techniques or the like, along a circular trace 98 comprising an open end of the passage 90. It will be apparent that the passage 90, in the expanded position of the tube 56, is unvalved and substantially unobstructed.

The cuff 64 is of somewhat unusual design. The struts 92, which connect the conduit 60 and member 62 throughout most of the length of the tube 56, are absent adjacent the cuff 64. Accordingly, a portion 100 of the member 62 is free to move radially outwardly further than the remainder of the member 62. Accordingly, the portion 100 is capable of expanding into sealing engagement with the trachea 66 and acts as a cuff upon delivery of a pressurized gas into the annulus 88.

In order to collapse the tube 56, either during manufacture thereof or preparatory to use, air is pumped out of the annulus 88 through the groove 72, radial passage 74 and a valved conduit 102, as by connecting the conduit 102 to a suitable vacuum pump (not shown). The tube 56 accordingly collapses to the configuration shown in FIG. 7. Suitable retaining strips (not shown) of cellophane or the like may be used to hold the conduit 60 and outer member 62 in the collapsed position during shipment.

In use, the tube 56 is removed from suitable packaging (not shown). While the tube 56 is in the collapsed configuration, the anesthesiologist inserts the same into the trachea 66 of the patient. Air or any other suitable gas is then delivered through the valved conduit 102 to pressurize the annulus 88 and thereby expand the tube 56 into the configuration illustrated in FIGS. 6 and 8. Because pressurized gas delivered into the annulus 88 also expands the cuff 64, a seal is made against the trachea 66 contemporaneously with expansion of the tube 56. The anesthesiologist then connects the fitting 58 to a suitable mechanical respirator (not shown) and mechanical breathing is commenced.

It will be evident that the reduced diameter of the collapsed tube 56 facilitates the insertion hereof into the trachea 66. As is apparent in FIGS. 6 and 8, the fluid passage 90 is of substantial size to accommodate the required volume of air for respiration purposes.

The same principles discussed previously in connection with the endotracheal tubes 10, 56 apply to urethral catheters, the only difference in the devices is that endotracheal tubes are shorter and have larger diameters for apparent reasons. In use, the cuffs of urethral catheters are normally inflated with a liquid, usually water, rather than air. Also, the urethral catheter is normally used only to drain the bladder so that all fluid flow is outwardly through the tube rather than alternately in and out.

It will be understood that while the invention has been described specifically with reference to a small number of embodiments, various changes and modifications may be made within the full and intended scope of the appended claims.

I claim:

1. A tube which may be collapsed for insertion of a first end into a body passage and then expanded for transporting a fluid, comprising
    an elongate conduit, open at each end, providing an intermediate section between the ends having thin inner and outer walls defining an annulus therebetween closed at the first tube end, the conduit being expandable from a collapsed configuration to a distended configuration in response to the introduction of fluid into the annulus;
    means at least partially rigidifying the conduit in the collapsed configuration thereof comprising a plurality of generally parallel pleats in the inner and outer walls extending from adjacent from adjacent the first conduit end toward the second conduit end providing spaced transversely corrugated inner and outer walls; means for delivering fluid to the annulus; and
    an expandible cuff on the exterior of the tube for expansion into sealing engagement between the tube exterior and the interior of the body passage.

2. The tube of claim 1 wherein the pleats of the inner and outer tubes are of similar configuration and, in the collapsed configuration, nest.

3. The tube of claim 2 wherein the material of the conduit provides a memory of a normal distended configuration expanded transversely of the longitudinal axis of the tube.

4. The tube of claim 2 wherein the cuff comprises a diaphragm sealed to the exterior of the tube providing an inflatable cuff annulus and a member providing a passage independent of the conduit and independent of the annulus defined between the inner and outer walls for selectively and independently admitting and exhausting fluid from the cuff annulus.

* * * * *